United States Patent [19]

Enrico

[11] 4,232,157
[45] Nov. 4, 1980

[54] PROCESS FOR PREPARING LYSERGOL DERIVATIVES

[76] Inventor: Corvi M. Enrico, Via Scalabrini 49, 29100 Piacenza, Italy

[21] Appl. No.: 26,685

[22] Filed: Apr. 3, 1979

[30] Foreign Application Priority Data

Apr. 5, 1978 [IT] Italy ............................... 22011 A/78

[51] Int. Cl.³ .......................................... C07D 457/02
[52] U.S. Cl. ...................................................... 546/68
[58] Field of Search .......................................... 546/68

[56] References Cited

U.S. PATENT DOCUMENTS

| | | | |
|---|---|---|---|
| 3,228,943 | 1/1966 | Bernardi et al. | 546/68 |
| 3,879,554 | 4/1975 | Temperilli et al. | 546/68 |
| 3,966,739 | 6/1976 | Bernardi et al. | 546/68 |

*Primary Examiner*—Mary C. Lee
*Attorney, Agent, or Firm*—Murray and Whisenhunt

[57] ABSTRACT

A novel process is disclosed for the preparation of derivatives of lysergol having the general formula:

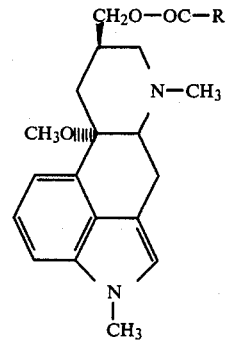

According to this process lysergol is directly used as the starting compound and, after the methylation at the 1 position of the corresponding 10 alpha-methoxy-lumilysergol, the methylated compound is directly esterified with a carboxylic acid R—COOH, the acid being selected in the group comprising aliphatic, cycloaliphatic, aromatic, and heterocyclic carboxylic acids, containing up to 10 carbon atoms.

7 Claims, No Drawings

PROCESS FOR PREPARING LYSERGOL DERIVATIVES

The invention relates to a novel process for the preparation of derivatives of lysergol, more particularly derivatives of 1-methyl-10-methoxy-lumilysergol, having the following general formula (I):

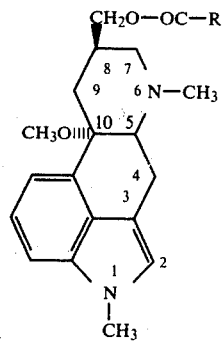

wherein R is a radical of an organic carboxylic acid, of the group comprising aliphatic, cycloaliphatic, aromatic and heterocyclic carboxylic acids, containing up to 10 carbon atoms and possibly halogen substituted.

The compounds represented by the formula (I) are endowed with interesting pharmacological properties, such as a remarkable adrenolytic and antiserotoninic activity.

The above derivatives are prepared, according to the prior art, starting from commercially available monohydrate lysergic acid, through the following reaction sequence:

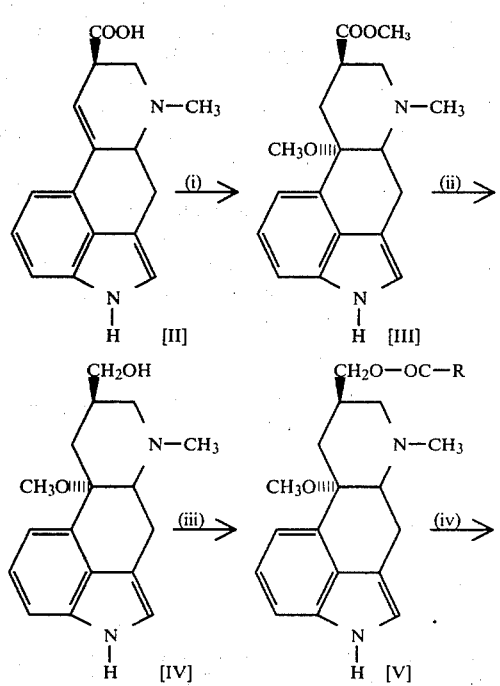

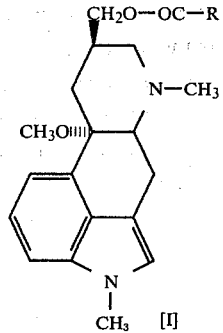

According to step (i), lysergic acid (II) is coverted to the corresponding 10-methylether-methylester (III), by irradiating with U.V. light a solution of the compound (II) in methanol containing concentrated $H_2SO_4$.

Thereafter 10-methoxy-lumilysergol (IV) is obtained by reducing the ester (III) with $LiAlH_4$ in tetrahydrofurane.

The alcohol (IV) is esterified through the treatment with a derivative of a carboxylic acid R—COX, such as acyl chlorides (X=Cl) or the corresponding anhydrides (X=O—OC—R), in the presence of a tertiary base, e.g. pyridine and triethylamine. Then the esters (V), thus obtained, are alkylated at the 1 position with methyl iodide in liquid ammonia and in the presence of $NaNH_2$ or $KNH_2$, to give the desired compound (I), (the 1-methylation being also possible even before the esterification step (iii)).

The above described reaction pattern is disclosed in the Belgian xxxx Pat. No. 633,430, in the French Pat. No. 2,084,678 and in the U.S. Pat. No. 3,228,943.

According to a modification of the general reaction pattern, relating to the step (iii), the French patent claims an alternative esterification process, as illustrated by the following scheme:

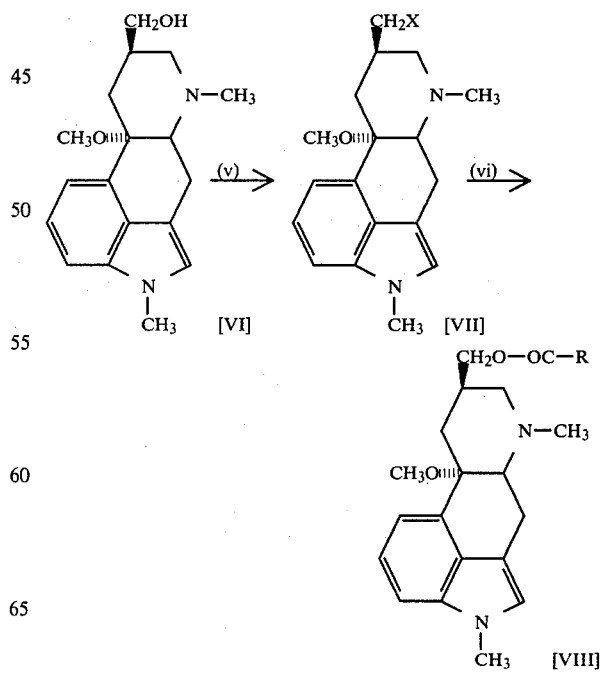

Such a modification is necessary when R is a radical comprising furane and pyrrolic rings which, as it is well known, are not stable in the presence of standard chlorinating agents, such as thionyl chloride and phosphorous oxychloride. In this case, since it is impossible to convert the acid RCOOH to the corresponding halides RCOX (X=Cl), the alcohols (VI) are converted to the alkyl chlorides (VII) through the treatment with tosyl chloride in pyridine and in the presence of pyridine hydrochloride (step V).

The compounds (VII) are reacted with the metal salts RCOO$^-$M$^+$ of the suitable carboxylic acids to give the compounds (VIII) (step vi).

According to the present invention, there has been found a novel process for preparing the compounds of formula (I), which is efficacious, simplified and of general use with respect to the meaning of the substituents R.

The process of the present invention for the preparation of derivatives of 1-methyl-10-methoxy-lumilysergol having the general formula (I), wherein R has the meanings already referred to, comprises the following step:

(a) converting lysergol (IX) to 10-alpha-methoxy-lumilysergol (X) through the irradiation of a solution of lysergol;

(b) methylating the compound (X) at the indole nitrogen atom by means of a methylating agent, the 1-methyl derivative being thus obtained;

(c) reacting the alcohol (XI) with a carboxylic acid R-COOH, wherein R has the above mentioned meaning, in molar excess with respect to the alcohol.

The lysergol is the starting reactant of the synthesis reaction and is a natural product, which can be easily obtained by extracting seeds of some species of Ipomoea.

The use of such a raw material has some important advantages over the use of lysergic acid, since lysergol does not undergo isomerization at the C-8 position and does already possess the chemical function ready for the esterification.

The reaction pattern of the process of the invention is represented as follows:

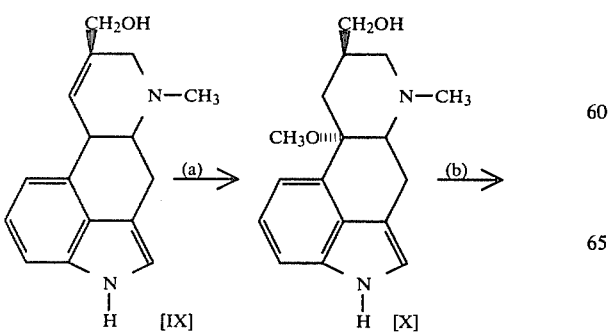

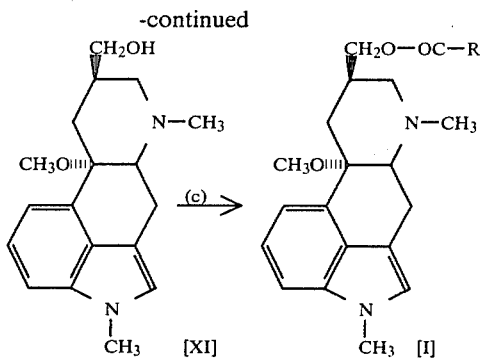

According to the preferred embodiment, lysergol (IX) is dissolved in methanol containing concentrated sulfuric acid, at the ratio of 5 to 20% v/v and subjected to the rays of an U.V. lamp of the mercury discharge type or the like.

The reaction is carried out in an inert gas atmosphere and at a temperature of between 10° C. and 50° C.

The 10 alpha-methoxy-lumilysergol (X) is isolated with good yields after standard processing of the reaction mixture. In the step (b) of the present process, the methylation at the indole nitrogen atom is effected by treatment of the solution of the compound (X) in dimethylsulfoxide with methyl iodide, in the presence of a finely ground alkali hydroxide at a temperature of between 10° C. and 40° C.

At the end of the reaction, the reaction mixture is diluted with water and the 1-methyl-10 alpha-methoxy-lumilysergol (XI) is extracted by means of suitable organic solvents, such as chloroform. Then, in the step (c), the alcohol (XI) is dissolved in tetrahydrofurane and the resulting solution is supplemented with the carboxylic acid, in the amount of 2 to 4 moles per mole of the alcohol (XI), together with a slight excess of dicyclohexylcarbodiimide as the condensating agent.

The reaction is carried out at a temperature of between 20° and 40° C. and, at the end of the esterification, the dicyclohexylurea is separated by filtration, the excess of unreacted acid R—COOH is recovered and the reaction product (I) is obtained through the evaporation of the solvent under reduced pressure.

The esterification method of the process of the present invention permits the carboxylic acids to be directly used, without being previously converted to functional derivatives, such as the corresponding acid chlorides, anhydrides and metal salts, thus eliminating the problems and disadvantages of the prior art.

The following examples illustrate the experimental details of the process of the present invention, without having any limiting purpose.

EXAMPLE 1

1-methyl-10 alpha-methoxy-lumilysergol-8(5'-bromo) nicotinate:

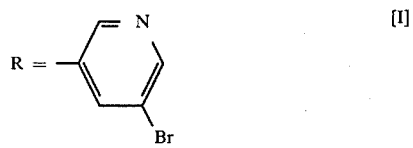

(a) 10 alpha-methoxy-lumilysergol (X) 50.35 g of lysergol are dissolved in 1500 mls of a mixture CH$_3$OH/H$_2$SO$_4$ (40/7.5 v/v), possibly heating the mixture to 35°–40° C.

The solution is charged in a suitable reactor for photochemical reactions, and the irradiation is started, the temperature being maintained at 20°–40° C. and the atmosphere being of an inert gas. The light source is a Phillips lamp HPLR-N 250W.

The behaviour of the reaction is controlled by thin layer chromatography (TLC), by using Silicagel GF$_{254}$ as the adsorbant, the mixture CH$_3$OH/CHCl$_3$/NH$_4$OH = 20/80/0.2 as the eluant, and U.V. light ($\lambda$=254 nm) and the Van Urk reagent (Stahl No. 73) as the revealing means.

At the end of the reaction the contents of the reactor are poured into 6 liters of ice water, the mixture is made alkaline with NH$_4$OH (650 mls) and extracted until exhausted with chloroform. The combined organic extracts are washed with water, dried over Na$_2$SO$_4$, filtered and concentrated to a residue under reduced pressure and at 30°–35° C.

The residue is crystallized again from acetonitrile, there being obtained 45 g (yield=80%) of 10 alpha-methoxy-lumilysergol, m. p. 183°–185° C.

(b) 1-methyl-10 alpha-methoxy-lumilysergol (XI)

30.5 g of dry, finely ground KOH and 250 mls of dimethylsulfoxide are charged in a reactor having mechanical stirrer, thermometer and cooling means.

The mixture is stirred for 10 minutes and then added with 39 g of 10 alpha-methoxy-lumilysergol (X): the stirring is continued at 15°–20° C. for 45 minutes and then 9.8 mls of CH$_3$I are added dropwise, the temperature being controlled at 25° to 35° C. Upon this addition is completed, the reaction mixture is stirred for about 45 minutes, the reaction behaviour being monitored by TLC under the same conditions as in the step (a).

The contents of the reactor are poured in ice water, the precipitate is filtered and the filtration liquors are exhausted by subsequent extractions with CHCl$_3$.

The combined organic solutions are washed with water, and then dried over Na$_2$SO$_4$, filtered and concentrated to a residue under reduced pressure at 30° C. The raw residue is combined with the precipitate from water and crystallized again from acetone. There are obtained 28–30 g (yield=about 70%) of 1-methyl-10 alpha-methoxy-lumilysergol, m.p. 213°–216° C.

(c) 1-methyl-10 alpha-methoxy-lumilysergol-8 (5'-bromo) -nicotinate

A solution comprising 79.4 g of 5-bromo-nicotinic acid, 27.05 g of 1-methyl-10 alpha-methoxy-lumilysergol (XI) and 900 mls of tetrahydrofurane is prepared in a reactor provided with thermometer, stirrer and cooler.

There are added 20.62 g of dicyclohexylcarbodiimide, the temperature being maintained at about 30° C.

The reaction is monitored by TLC under the same conditions above referred to.

The mixture is cooled to 0° C., the precipitated dicyclohexylurea is separated by filtration and the filtrate is concentrated to a residue under reduced pressure at 35° C.

The residue is taken with 800 mls of CH$_2$Cl$_2$ and the mixture is treated under stirring with a saturated water solution of NaHCO$_3$, to recover the unreacted 5-bromo-nicotinic acid.

After separation of the phases, the organic phase is washed with water, dried over Na$_2$SO$_4$, filtered and concentrated to dryness under pressure at 30° C.

The residue is crystallized again from ether.

There are obtained 40 g (yield=about 90%) of bromo-nicotinic ester of 1-methyl-10 alpha-methoxy-lumilysergol, m.p. 135°–136° C. The alkaline aqueous phase is made acidic to pH 3 with HCl and the unreacted bromo-nicotinic acid is recovered by filtration (recovery yield=about 75%).

EXAMPLE 2

1-methyl-10 alpha-methoxy-lumilysergol-8-nicotinate $$R = -\left\langle\underset{\phantom{x}}{\overset{N}{\phantom{x}}}\right\rangle \quad [\text{I}]$$

The starting 1-methyl-10 alpha-methoxy-lumilysergol is prepared as described in the Example 1, through the steps (a) and (b), and the esterification is carried out under experimental conditions like those of the step (c), by using 48.3 g of nicotinic acid, 27.04 g of the compound (XI), 750 mls of tetrahydrofurane and 20.62 of dicyclohexylcarbodiimide.

At the end of the process, there are obtained 32 g (yield=88%) of pure ester, m.p. 124°–126° C.

The recovery yield of the unreacted nicotinic acid is about 73%.

EXAMPLE 3

1-methyl-10 alpha-methoxy-lumilysergol-8-(2'-furan)-carboxylate $$R = -\left\langle\underset{O}{\phantom{x}}\right\rangle \quad [\text{I}]$$

In this case too, the desired ester is prepared according to the operating conditions of Example 1.

More particularly, the esterification reaction is carried out by using 13.5 g of the compound (XI), 10.3 g of dicyclohexylcarbodiimide, 250 mls of THF and 20.34 g of pyromucic acid (2-furoic acid). At the end, there are obtained 16 g (yield=90%), of the ester, m.p. 142°–144° C.

The recovery yield of the unreacted furan-2-carboxylic acid is about 40%.

I claim:

1. A process for preparing a compound of the formula:

$$\text{(I)}$$

[structure showing CH$_2$O—OC—R group at position 7/8, with numbered ring positions 1-10, N—CH$_3$ at position 6, CH$_3$O at position 10, and N—CH$_3$ at position 1]

wherein R is the radical of an organic carboxylic acid selected from the group consisting of nicotinic acid, 5-bromo-nitocinic acid and 2-furoic acid, said process comprising:

(a) converting lysergol, having the formula:

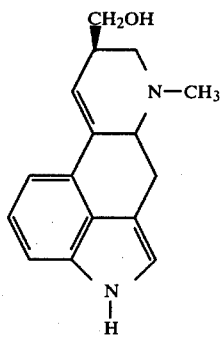

to 10-alpha-methoxy-lumilysergol of the formula:

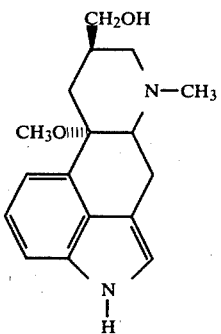

by irradiation with U. V. rays:

(b) methylating the compound (X) at the indole nitrogen atom by means of a methylating agent to obtain the 1-methyl derivative of the formula:

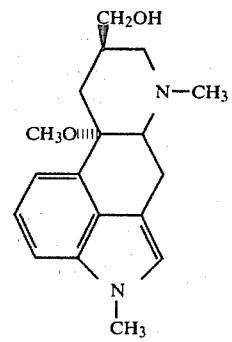

(c) reacting the alcohol (XI) with a molar excess of an organic carboxylic acid of the formula R—COOH, wherein R is defined above, to obtain the compound (I).

2. Process according to claim 1, wherein R is a radical of 5-bromo-nicotinic acid.

3. Process according to claim 1, wherein step (a) is conducted on a solution of lysergol in a mixture of methanol and sulfuric acid containing about 5 to about 20% by volume of sulfuric acid in an inert gas atmosphere using mercury discharge U. V. lamps or equivalent types at a temperature of between about 10° and about 50° C., and step (b) is conducted using methyl iodide as the methylating agent in the presence of dry, finely ground alkali hydroxides, in the presence of dimethylsulfoxide as the solvent and at a temperature of between about 10° and about 40° C., and step (c) is conducted in tetrahydrofurane using an excess of said carboxylic acid of between 2 and 4 times the stoichiometric amount and in the presence of dicyclohexylcarbodiimide as the condensing agent.

4. A process according to claim 3, wherein said carboxylic acid is 5-bromo-nicotinic acid.

5. A process according to claim 1, characterized in that the photochemical reaction is effected on a solution of lysergol in a mixture of methanol and sulfuric acid (containing 5 to 20% $H_2SO_4$ v/v), in an atmosphere of an inert gas, by using mercury discharge U.V. lamps or of equivalent type, at a temperature of between 10° and 50° C.

6. A process according to claim 1, characterized in that the reaction of methylation at 1 position of the 10 alpha-methoxy-lumilysergol is carried out with methyl iodide, in the presence of dry, finely ground, alkali hydroxides, dimethylsulfoxide being the solvent and the temperature being of between 10° and 40° C.

7. A process according to claim 1, characterized in that the esterification reaction of the 1-methyl-10 alpha-methoxy-lumilysergol is carried out in tetrahydrofurane, by using an excess of carboxylic acid of between two and four times with respect to the stochiometric amount, and in the presence of dicyclohexylcarbodiimide as the condensing agent.

* * * * *